United States Patent
Kim et al.

(10) Patent No.: US 10,437,440 B2
(45) Date of Patent: Oct. 8, 2019

(54) ANALYTIC DATA EXPORT TOOL

(71) Applicant: salesforce.com, inc., San Francisco, CA (US)

(72) Inventors: Yuseung Kim, San Francisco, CA (US); Qingqing Liu, Dublin, CA (US)

(73) Assignee: salesforce.com, inc., San Francisco, CA (US)

( * ) Notice: Subject to any disclaimer, the term of this patent is extended or adjusted under 35 U.S.C. 154(b) by 378 days.

(21) Appl. No.: 15/052,580

(22) Filed: Feb. 24, 2016

(65) Prior Publication Data

US 2017/0070557 A1  Mar. 9, 2017

Related U.S. Application Data

(60) Provisional application No. 62/214,570, filed on Sep. 4, 2015.

(51) Int. Cl.
| | | |
|---|---|---|
| *G06F 17/00* | (2019.01) | |
| *G06F 3/048* | (2013.01) | |
| *G06Q 40/04* | (2012.01) | |
| *G06F 3/0484* | (2013.01) | |
| *G06F 3/0482* | (2013.01) | |
| *G06Q 10/06* | (2012.01) | |
| *H04L 29/08* | (2006.01) | |
| *G16H 40/20* | (2018.01) | |

(52) U.S. Cl.
CPC ........ *G06F 3/04842* (2013.01); *G06F 3/0482* (2013.01); *G06Q 10/063* (2013.01); *G06F 2216/03* (2013.01); *G16H 40/20* (2018.01); *H04L 67/12* (2013.01); *H04L 67/22* (2013.01); *H04L 2209/60* (2013.01)

(58) Field of Classification Search
CPC ........ G06F 3/0481; G06F 8/38; G06F 9/4443; H04L 2209/60; H04L 67/12
See application file for complete search history.

(56) References Cited

U.S. PATENT DOCUMENTS

| | | | | |
|---|---|---|---|---|
| 6,195,662 B1 * | 2/2001 | Ellis | ............ | G06F 17/2264 |
| | | | | 707/999.001 |
| 6,792,615 B1 * | 9/2004 | Rowe | ............ | G11B 27/031 |
| | | | | 348/E5.108 |
| 2004/0133876 A1 * | 7/2004 | Sproule | ............ | G06Q 10/063 |
| | | | | 717/105 |
| 2008/0270340 A1 * | 10/2008 | Abrams | ............ | G06F 17/30563 |
| 2012/0218254 A1 * | 8/2012 | Abeln | ............ | G06T 19/00 |
| | | | | 345/419 |

(Continued)

*Primary Examiner* — Jordany Nunez
(74) *Attorney, Agent, or Firm* — Sterne, Kessler, Goldstein & Fox P.L.L.C.

(57) ABSTRACT

Disclosed herein are system, method, and computer program product embodiments for an analytic data export tool. An embodiment by visualizing, by a computing device, a plurality of available analytic data in a graphical user interface; receiving, by the computing device, a data selection input, wherein the data selection input comprises an interaction with the visualized plurality of available analytic data; packaging the plurality of available analytic data in a data package according to the data selection input; and exporting the data package according to one of a plurality of displayed export options displayed in the graphical user interface.

23 Claims, 9 Drawing Sheets

(56) References Cited

U.S. PATENT DOCUMENTS

| | | | |
|---|---|---|---|
| 2013/0257850 A1* | 10/2013 | Chen | G06T 19/20 345/419 |
| 2014/0181240 A1* | 6/2014 | Scott | H04L 67/06 709/217 |
| 2017/0091699 A1* | 3/2017 | Mueller | G06Q 10/083 |

* cited by examiner

ANALYTIC DATA EXPORT TOOL

BACKGROUND

Tools that allow exporting and sharing business analytic data in the business intelligence analytics industry do so by a variety of methods. However, these tools are designed and optimized for desktop platforms and large monitors with a mouse and keyboard input. This results in a lack of tools available to export and share business analytic data using a mobile platform as current tools are too resource intensive or lack a proper interface for a mobile tool. Due to this, users are only able export and share business analytic data when at a desktop environment, leaving them without anyway to export or share business analytic data while outside such an environment.

SUMMARY

Provided herein are system, apparatus, article of manufacture, method and/or computer program product embodiments, and/or combinations and sub-combinations thereof, for an analytic data export tool.

An embodiment includes a computer implemented method for exporting analytic data. The method operates by visualizing, by a computing device, a plurality of available analytic data in a graphical user interface. Further, the method also operates by receiving, by the computing device, a data selection input, wherein the data selection input comprises an interaction with the visualized plurality of available analytic data. The method may also comprise packaging the plurality of available analytic data in a data package according to the data selection input. Additionally the method operates by exporting the data package according to one of a plurality of displayed export options displayed in the graphical user interface.

Another embodiment includes a system for exporting analytic data. The system includes a memory and at least one processor coupled to the memory. The processor is configured visualize a plurality of available analytic data in a graphical user interface. Further, the processor is configured to receive a data, selection input, wherein the data selection input, comprises an interaction with the visualized plurality of available analytic data. The processor may also be configured package the plurality of available analytic data in a data package according to the data selection input. Additionally the processor may be configured to export the data package according to one of a plurality of displayed export options displayed in the graphical user interface.

A further embodiment includes a non-transitory computer-readable device having instructions stored thereon that, when executed by at least one computing device, cause the computing device to perform operations. The operations include visualizing a plurality of available analytic data in a graphical user interface. Further, the operations may also include receiving a data selection input, wherein the data selection input comprises an interaction with the visualized plurality of available analytic data. The operations may also comprise packaging the plurality of available analytic data in a data package according to the data selection input. Additionally the operations include exporting the data package according to one of a plurality of displayed export options displayed in the graphical user interface.

BRIEF DESCRIPTION OF THE DRAWINGS

The drawing are representative of embodiments of the invention. In the drawings, like reference numbers generally indicate identical or similar elements. Additionally, generally, the left-most digit(s) of a reference number identifies the drawing in which the reference number first appears.

DETAILED DESCRIPTION

Provided herein are system, method and/or computer program product embodiments, and/or combinations and sub-combinations thereof, for exporting analytic data.

Figure 1:
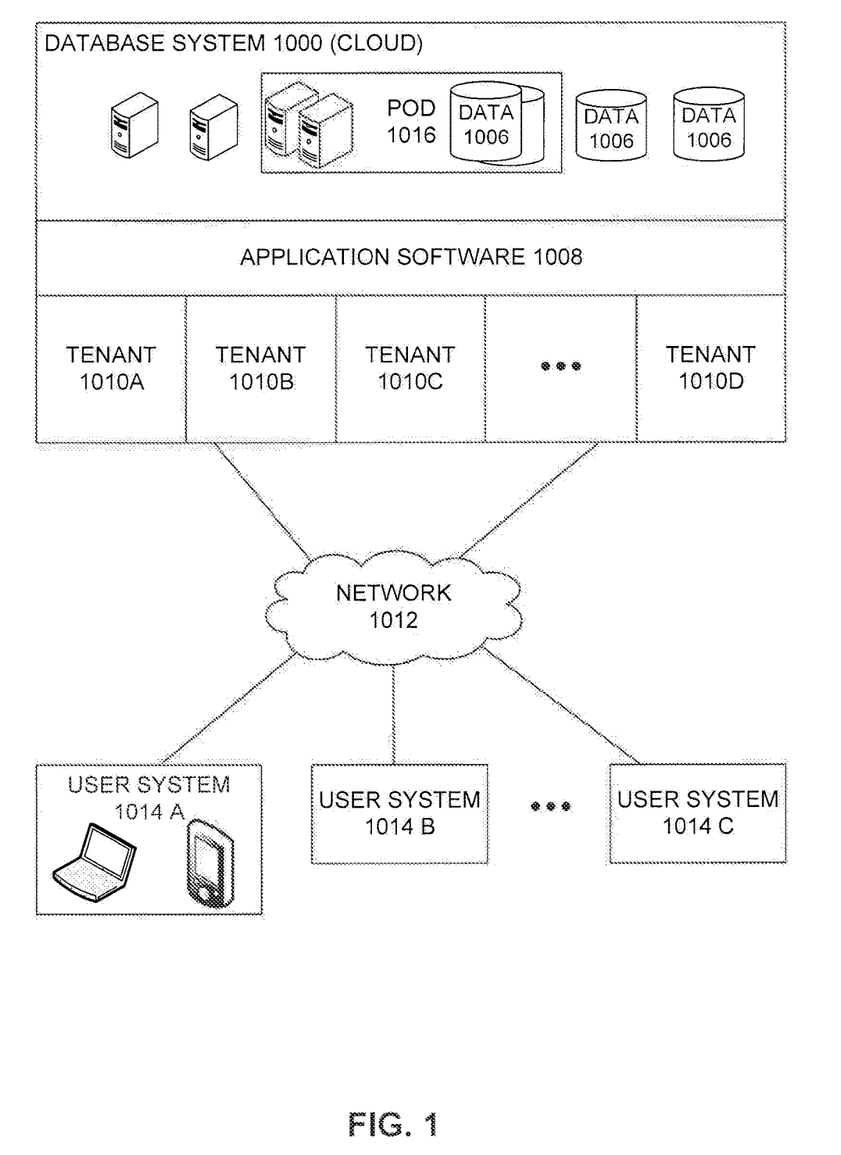
FIG. 1 shows an example database system according to some embodiments.

FIG. 1 shows an example database system 1000 used in accordance with some embodiments. Database system 1000 may include different application servers 1002 and databases 1004 connected together by networking equipment. Different combinations of application servers 1002 and data servers may execute different application software 1008 and access data 1006 stored in databases 1004.

User systems 1014 connect to application servers 1002 and databases 1004 through a network 1012. Network 1012 and the networks connecting together application servers 1002 and databases 1004 may include any combination of local area networks (LANs), wide area networks (WANs), telephone networks, wireless networks (Wi-Fi), cellular networks, or the like, or any combination thereof. Database system 1000 and user systems 1014 may operate within a private enterprise network and/or may operate within a publically accessible web-based network.

User systems 1014 may include desktop computers, personal computers (PCs), work stations, laptop computers, tablet, computers, handheld computing devices, mobile cellular phones, smartphones, terminals, or any other device capable of accessing network 1012 and database system 1000. User systems 1014 use different protocols to communicate with database system 1000 over network 1012, such as transfer control protocol and Internet protocol (TCP/IP), hypertext transfer protocol (HTTP), and/or file transfer protocol (FTP). In one example, user systems 1014 may operate a web browser or operate applications for sending and receiving HTTP signals to and from an HTTP server operating in database system 1000.

Database system 1000 in conjunction with application software 1008 may provide an almost limitless variety of different services, such as providing software as a service (SaS), customer relationship management (CRM), enterprise resource planning (ERP), file sharing, web-based commerce, social networking, cloud-based computing and/or storage, or the like, or any combination thereof. Database system 1000 and/or network 1012 are alternatively referred to as the Internet, the cloud, and/or a cloud based computing system.

Multi-Tenant System

In one example, database system 1000 and application software 1008 may operate as a multi-tenant system (MTS). A multi-tenant system refers to a database system where different hardware and software are shared by one or more organizations represented as tenants 1010. For example, database system 1000 may associate a first tenant 1010A with an organization that sells airline services, associate a second tenant 1010B with an organization that sells widgets, and associate a third tenant 1008C with an organization that sells medical administration services. The multi-tenant system effectively operates as multiple virtual databases each associated with one of tenants 1010.

A pod 1016 may include groups of application servers 1002 and databases 1004 that share an instance of the multi-tenant system. Different pods 1016 may operate independently but may share some processing equipment, such as routers and storage area networks (SANs). For example, tenants 1010B and 1010C may operate within pod 1016 and a user associated with tenant 1010C may use user system 1014A to access the multi-tenant system operating in pod 1016. User system 1014A sends requests from the user to a load balancer in pod 1016 and the load balancer forwards the requests to one of application servers 1002 within pod 1016. Application server 1002 services the requests by executing application software 1008 within pod 1016 and/or accessing data 1006 from databases 1004 within pod 1016.

Database system 1000 may include hundreds of pods 1016 and a database administrator may assign thousands of tenants 1010 to the same pod 1016. The database administrator may add new pods 1016 for servicing additional tenants 1010 or may reassign tenants 1010 to different pods 1016. For example, one of tenants 1010 may use a relatively large amount of processing bandwidth and/or use a relatively large amount of storage space. The database administrator may reassign that tenant 1010 to a different pod 1016 with more processing and/or storage bandwidth. Thus, the multi-tenant system may scale for almost any number of tenants and users.

Figure 2:
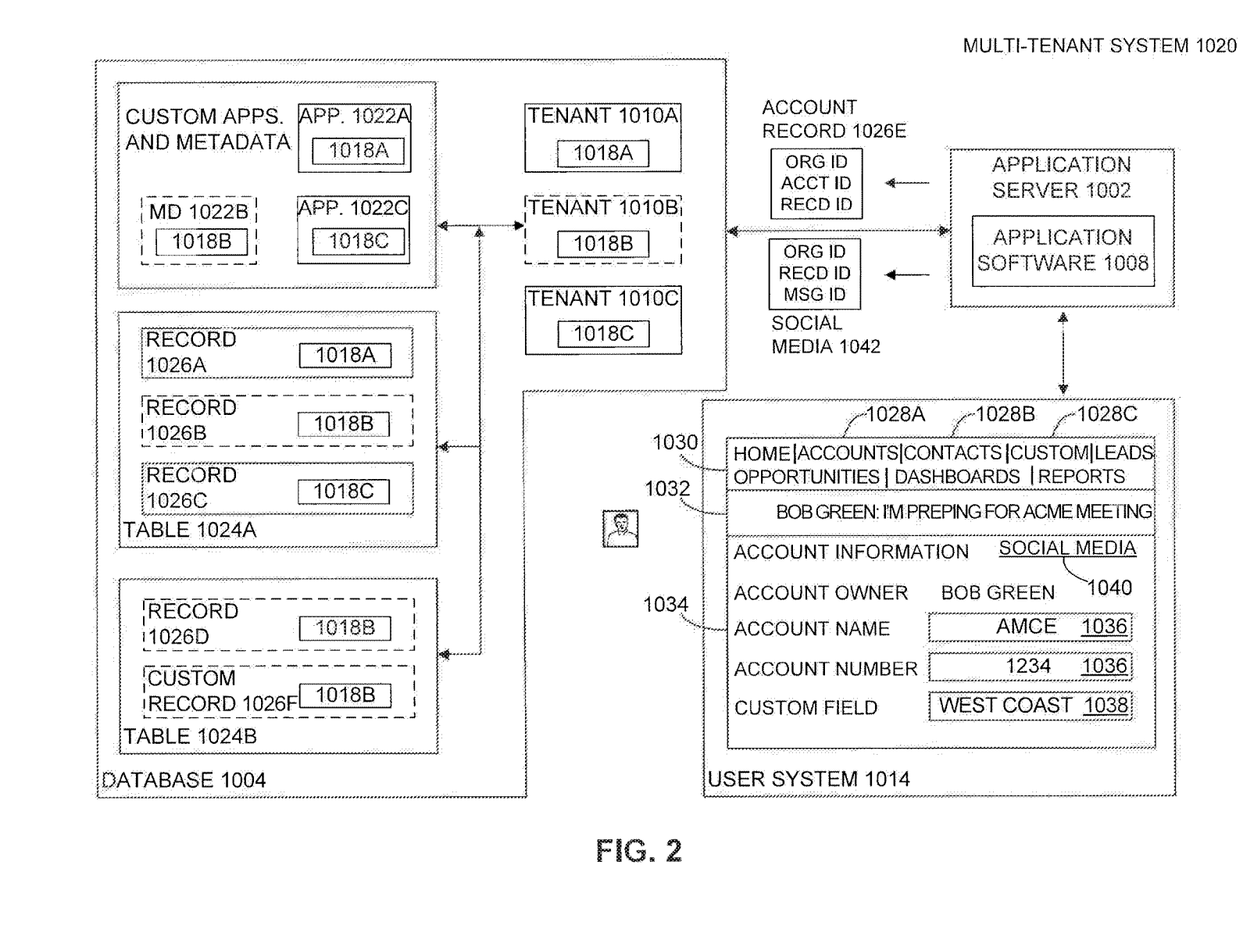
FIG. 2 shows an example multi-tenant system according to some embodiments.

FIG. 2 shows a platform for a multi-tenant system (MTS) 1020 that may operate within database system 1000 of FIG. 1. Multi-tenant system 1020 may comprise a collection of objects. The objects may refer to entities such as users, tenants, accounts, contacts, leads, opportunities, reports, cases, files, documents, orders, price books, products, solutions, forecasts, or any other definable category. Objects also may refer to instances of the entities such as the data for the individual users, tenants, accounts, contacts, leads, opportunities, reports, cases, etc.

Objects also may refer to tables 1024 that include fields or a schema describing the entities. For example, table 1024A may define fields for customer contacts such as name, address, phone number, fax number, etc. The same or another table 1024B may define fields for purchase orders such as customer, product, sale price, date, etc. Objects also may refer to records 1026 that contain data or instances for the entities and fields. For example, record 1026A may contain the specific name, address, phone number, fax, number, etc. for a particular customer contact and record 1026C may contain the specific customer, product, sale price and date for a particular purchase order.

Multi-tenant system 1020 may use identifiers to maintain relationships between different objects. For example, application software 1008 may assign unique organization identifiers (org ids) 1018A, 1018B, and 1018C to tenants 1010A, 1010B, and 1010C, respectively. Application software 1008 then associates other objects with org ids 1018.

For example, a user may log into multi-tenant system 1020 via user system 1014. Application software 1008 accesses one of tables 1024 that associates a password for the user with tenant 1010B. Application software 1008 then identifies different records 1026B, 1026D, and 1026F associated with org id 1018B and displays data from records 1026B, 1026D, and 1026F to the user via user system 1014. Application programmer interfaces (APIs) also may access data in multi-tenant system 1020 via user system 1014 in a same manner as users to maintain similar security protocols and access privileges.

In one example, application software 1008 may display a toolbar 1030 identifying different entities 1028 associated with tenant 1010B. The user may select tabs in toolbar 1030 to view, edit, and/or create instances (data) of entities 1028. For example, the user may select a tab associated with accounts entity 1028A and select options for creating a new account 1034. The user enters data for new account 1034 into fields 1036 and application software 1008 creates a record 1026E containing the data. Application software 1008 assigns record 1026E org id 1018B for tenant B, an account identifier (acct id), and a record identifier (reed id) before storing record 1026E in one of tables 1024.

Multi-tenant system 1020 may establish relationships between different entities 1028. For example, the user may associate different contacts 1028B with account 1034. The user may select a tab in toolbar 1030 associated with contacts 1028B and enter contact, information for a customer. Application software 1008 creates another record 1026 containing the contact information that includes the record id for account 1034. Users accessing account 1034 can then also view associated contacts 1028B.

Multi-tenant system 1020 enable users to create custom metadata 1022B for tenant specific functions, objects, entities, categories, and/or data. For example, an administrator for tenant 1010B, or a third party vendor, may create a custom entity 1028C with a unique combination of fields 1036 and 1038. Application software 1008 creates metadata 1022B defining custom entity 1028C and then accesses metadata 1022B enabling users for tenant 1010B to view, edit, and create custom records 1026F for custom entity 1028C.

Multi-tenant system 1020 also enable users to create and execute custom application software 1022A and 1022C. For example, the organization associated with tenant 1010C may provide medical administration services. The administrator for tenant 1010C, or a third party vendor, may create custom application software 1022C that generates medical reports and/or manages medical records. Application software 1008 associates custom application software with org id 1018C allowing users for tenant 1010C to access custom application software 1022C and generate and/or manage the medical reports and, records.

In some embodiments, multi-tenant system 1020 may associate users with user profiles and assign the users unique user identifiers (user ids). The user profiles may include a collection of data, about a user, such as a name, a title, a phone number, a photo, a biographical summary, or a status. Multi-tenant system 1020 also may associate the users with permission profiles that determine which records 1026 and application software 1008 and 1022 the users may access. For example, a permission profile for a first user may allow access to data and software for a salesperson and a permission profile for a second user may allow access to data and software for an administrator.

A group may refer to a collection of users within an organization. In some embodiments, a group may include users with a similar attribute or a similar membership or subscription. Multi-tenant system 1020 may assign groups of users unique group identifiers (group ids) and provide the groups various visibilities. For example, some groups may be private while others may be public. To become a member within a private group, users may request subscription to the group and acceptance by an administrator or group owner.

Social Networks

Multi-tenant system 1020 may associate social media with different records 1026. For example, a user may select an icon 1040 to post a message 1032 relating to account 1034. Application software 1008 generates social media data 1042 that includes, message 1032, org id 1018B for tenant 1010B, the record identifier for account 1034, and a unique message identifier (msg id). Users associated with tenant 1010B then may access account 1034, view associated message 1032, and create other related messages. For example, another user may access account 1034 and post a comment to message 1032. Application software 1008 creates additional social media data that includes the comment, org id 1018B for tenant 1010B, and the msg id for message 1032. Thus, users accessing account 1034 may not only view, edit, and/or create account 1034, but also may view and/or post social media, such as message 1032, associated account 1034.

Message 1032 is alternatively referred to as a feed item and may include any type of information viewable in a feed, such as user-generated textual posts or comments, documents, audio data, image data, video data, or any other type of data Feed items 1032 may include links or attach to other documents or files. Feed items 1032 may be associated via identifiers with one or more objects, entities, users, groups, records, or other feeds. Multi-tenant system 1020 also may transmit email notifications or other types of network communications to users associated with any object, entity, group, record, or feed.

More details regarding database system 1000, multi-tenant system 1020, and social networks are described in U.S. Pat. No. 7,730,478, titled METHOD AND SYSTEM FOR ALLOWING ACCESS TO DEVELOPED APPLICATIONS VIA A MULTI-TENANT ON-DEMAND DATABASE SERVICE, by Craig Weissman, issued on Jun. 1, 2010; U.S. Pat. No. 7,779,039, titled CUSTOM ENTITIES AND FIELDS IN A MULTI-TENANT DATABASE SYSTEM, by Weissman et al., issued on Aug. 17, 2010; and U.S. Pat. No. 8,478,722, titled ENTERPRISE LEVEL BUSINESS INFORMATION NETWORKING FOR CHANGES IN A DATABASE, by Peter Lee et al., issued on Jul. 2, 2013 which are all hereby incorporated by reference in its entirety and for all purposes.

Figure 3:
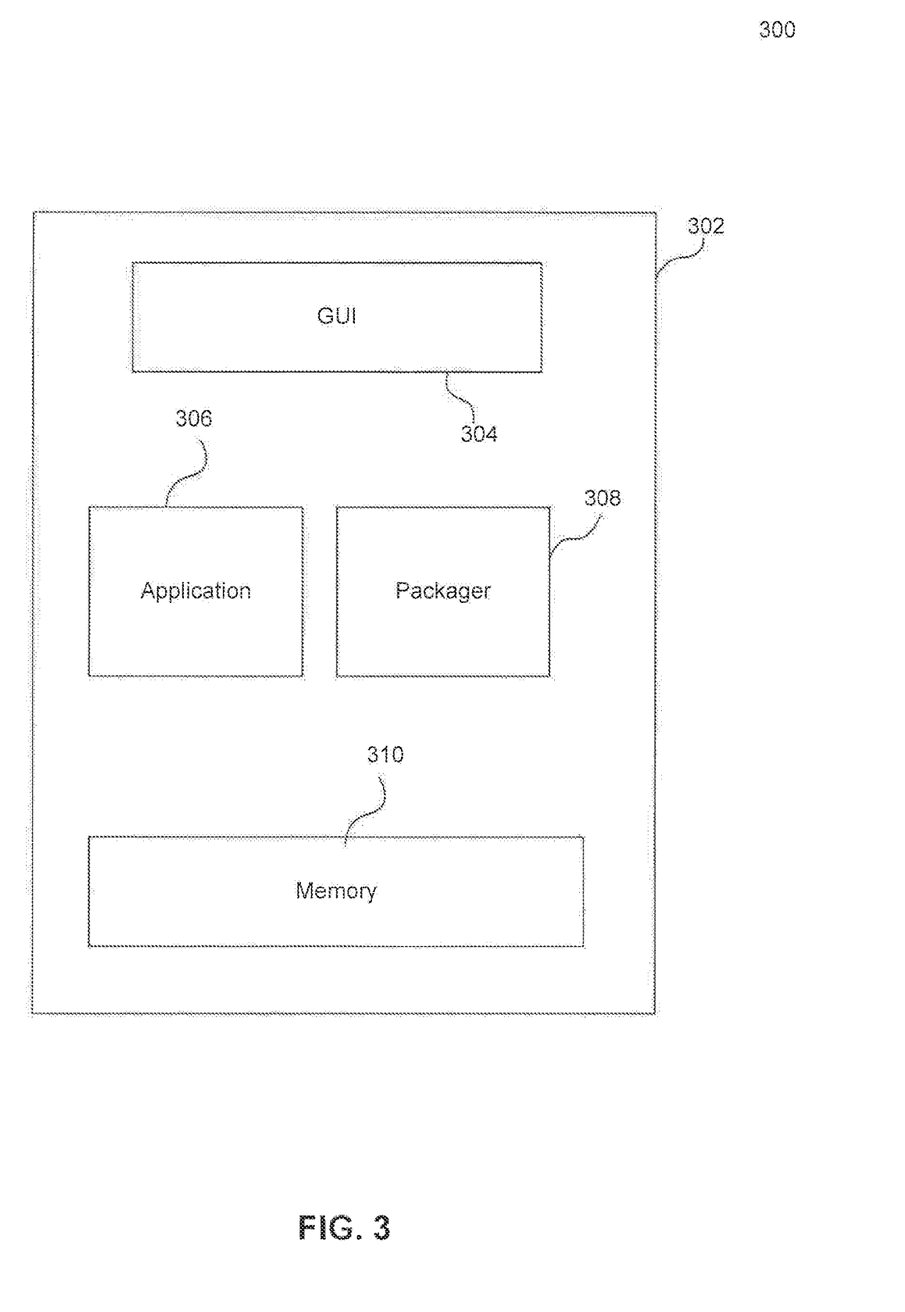
FIG. 3 shows an example block diagram of an analytic data exporting tool according to an embodiment.

FIG. 3 shows an example block diagram 300 of analytic data export tool 302, according to an embodiment. In an embodiment, analytic data export tool 302 may select, package, and export the analytic data of an application 306. According to some embodiments, analytic data export tool 302 comprises a graphical user interface (GUI) 304, packager 308, and memory 310.

According to another embodiment, analytic data export tool 302 may select, package, and export the analytic data of a plurality of applications.

In an embodiment, GUI 304 of analytic data export tool 302 may receive an export input. The export input may comprise an export request and may be received by GUI 304 as interactions with icons displayed in GUI 304, interactions with buttons displayed in GUI 304, interactions with information displayed in GUI 304, or any combination thereof, to name some examples. These interactions may comprise mouse clicks, mouse drags, gestures on a touch screen, or any combination thereof—to name a few.

According to an embodiment, once the export input is received, GUI 304 may display analytic data available for export within application 306. Analytic data may be determined to be available for export based upon the functionalities of application 306. In an embodiment, application 306 may comprise instructions stored on any non-transitory computer-readable device that, when executed by a computing device, collects, creates, stores, or modifies analytic data Analytic data may comprise datasets, tables, lists, lenses, dashboards, or any combination thereof—to name a few.

For example, GUI 304 may receive an export input as gestures on a touch screen. After the export input is received, GUI 304 may display the analytic data available for export within application 306, such as datasets and tables application 306 had formerly created and stored.

In an embodiment, GUI 304 may display the available analytic data for export within a plurality of applications.

According to an embodiment, while displaying the available analytic data, GUI 304 may receive an analytic data selection input as interactions with icons displayed in GUI 304, interactions with buttons displayed in GUI 304, interactions with information displayed in GUI 304, or any combination thereof—to name a few. These interactions may comprise mouse clicks, mouse drags, gestures made on a touch screen, or any combination thereof—to name a few. In an embodiment, the analytic data selection input comprises a selection of the available analytic data for export. For example, GUI 304 may display datasets and tables of application 306 that are available for export. Analytic data selection input may then comprise a selection of the datasets of application 306 available for export.

In an embodiment, GUI 304 may display a plurality of export options for the available analytic data of application 306. The plurality of export options may comprise protocols for exporting analytic data, programs for exporting data, applications for exporting data, or any combination thereof—to name a few. While displaying the plurality of export options, GUI 304 may receive an export option selection input as interactions with icons displayed in GUI 304, interactions with buttons displayed in GUI 304, or interactions with information displayed in GUI 304. These interactions may comprise mouse clicks, mouse drags, gestures made on a touch screen, or any combination thereof—to name a few. According to an embodiment, the export option selection may comprise a selection of an export option for exporting the analytic data selected by the analytic data selection input.

According to an embodiment, analytic data export tool 302 comprises a packager 308. In an embodiment, packager 308 may compile analytic data of application 306 selected by the analytic data selection input into a data package. The data package may comprise a plurality of datasets tables, lists, lenses, dashboards, or any combination thereof—to name a few. For example, the analytic data selection input may comprise a selection of the datasets of application 306 available for export. Packager 308 may then compile the datasets of application 306 into a data package.

In an embodiment, packager 308 may also covert the data package to a desired file format. The desired file format may comprise any format for data readable by a computer, such as BIN, DB, or DAT file formats, to name a few. According to an embodiment, packager 308 may further compress the converted data packed into a compressed file format such as 7Z, RAR, or ZIP, to, name some examples.

In an embodiment, analytic data export tool 302 comprises a memory 310. Memory 310 may store and recall analytic data for application 306. Memory 310 may be a Random-Access Memory (RAM), a Flash Memory, a Hard Drive, or a Solid State Drive—to name a few.

Figure 4:
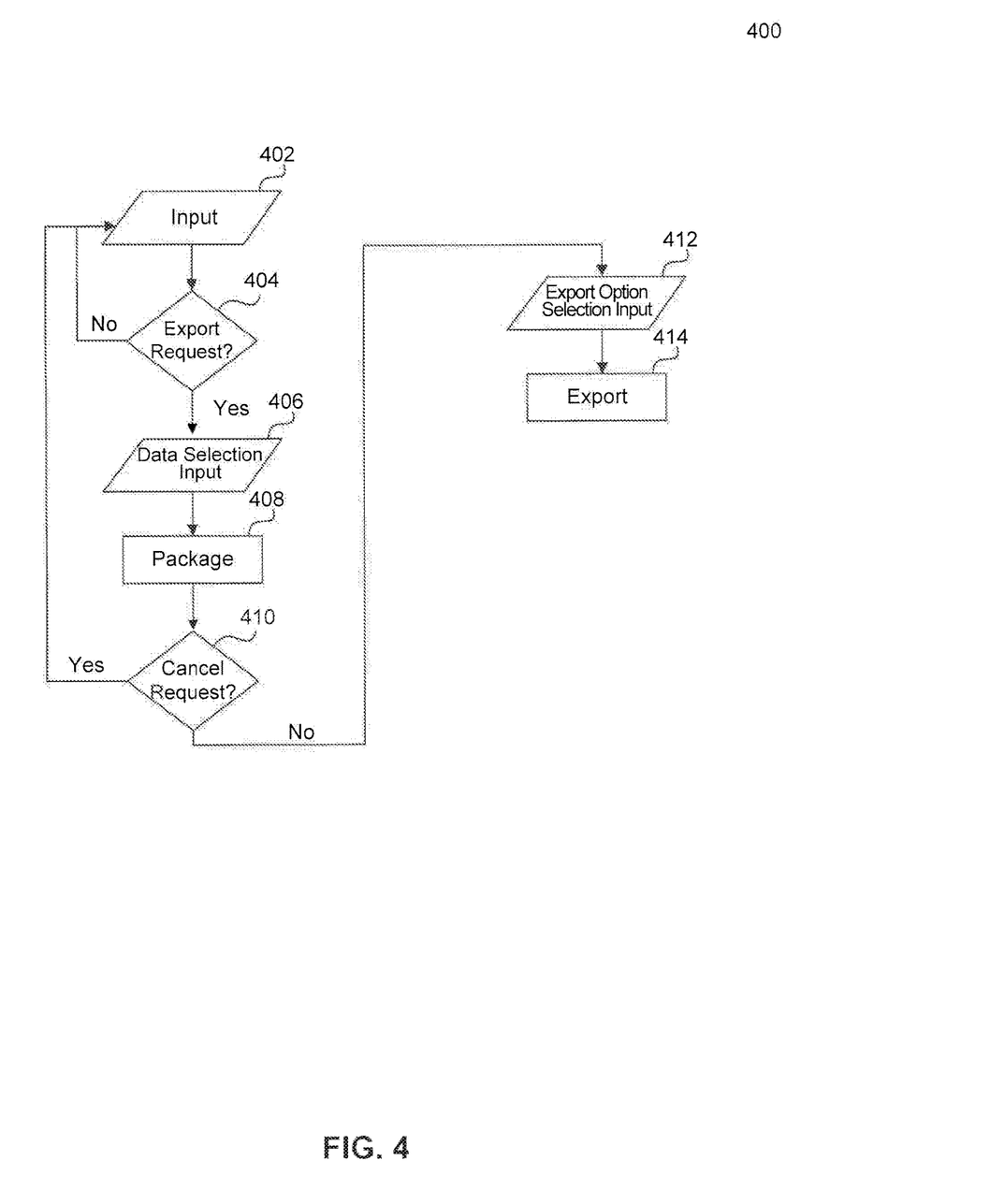
FIG. 4 shows an example flowchart illustrating, a process for exporting analytic data from an, application according to an embodiment.

FIG. 4 shows an example flowchart illustrating a process for exporting analytic data from an application 306 according to an embodiment.

At block 402, GUI 304 may receive an export input. For example, GUI 304 may receive an export input as a gesture made on a touchscreen. At block 404 analytic data export tool 302 evaluates whether the export input comprises an export request. If the input does not comprise an export request then block 402 is repeated. If the input does comprise an export request, then GUI 304 may visualize the analytic data available for export as interactive buttons and display these interactive buttons within an application 306. The available analytic data may be data that has been collected, created, or modified by application 306 and stored in memory 310 such as a plurality of datasets, tables, lists, lenses, and dashboards—to name a few. For example, GUI 304 may visualize and display datasets, tables, and lists created and stored by application 306 that are available for export.

According to an embodiment, GUI 304 may visualize and display the analytic data available for export as interactive buttons, text, figures, or any combination thereof.

In another embodiment, GUI 304 may visualize and display analytic data available for export with a plurality of applications. The available analytic data may be data that has been collected, created, or modified by the plurality of applications and stored in memory 310 such as a plurality of datasets, tables, lists, lenses, and dashboards to name a few. For example, GUI 304 may visualize and display datasets, tables, and lists created and stored by a plurality of applications that are available for export.

At block 406, while GUI 304 is displaying the available analytic data, GUI 304 may receive a data selection input. The data, selection input may comprise a selection of the analytic data available for export visualized and displayed by GUI 304. In an embodiment, GUI 304 may receive the data selection input as interactions with the analytic data available for export visualized and displayed by GUI 304, these interactions may comprise mouse clicks, mouse drags, gestures made on a touchscreen, or any combination thereof. For example, data selection input may comprise a selection of the datasets and tables of application 306 visualized and displayed by GUI 304.

At block 408 the analytic data displayed and visualized by GUI 304 is packaged by packager 308 according to the data selection input. Packaging the analytic data may comprise compiling the analytic data into a data package, converting the data package into a desired file format, and compressing the converted data package. For example, the analytic data of application 306 available for export may comprise a dashboard and a lens. At block 406, GUI 304 visualizes and displays the dashboard and lens and receives a data selection input that comprises a selection of the dashboard and lens. At block 408, packager 308 may compile the dashboard and lens into a data package comprising the dashboard and lens. Packager 308 may then convert the data package comprising the dashboard and lens into any desired file format and then compress the converted data package into any desired compressed file format.

At block 410, analytic data export tool 102 evaluates whether the data selection input comprises a cancel request. If the data selection input does not comprise a cancel request then the system continues to block 412, otherwise block 402 is repeated.

At block 412, GUI 304 displays a plurality of export options for the selected analytic data. The plurality of export options may comprise any export protocol native to the system such as e-mail, text message, applications, and cloud storage—to name a few. While displaying the plurality of export options, GUI 304 may receive an export option selection input that may be received by GUI 304 as interactions with the visualized and displayed export options, these interactions may comprise mouse clicks, mouse drags, gestures made on a touch screen, or any combination thereof—to name a few. The export option selection input may comprise a selection of an export option for the analytic data. For example, GUI may display export options of e-mail and text message and receive an export option selection input comprising a selection of e-mail.

At block 414, analytic export tool 102 will export the data according to the selection the export option selection input comprises. For example, at block 412, GUI 304 may display a plurality of export options comprising e-mail and text message. GUI 304 may then receive an export option selection input comprising a selection of e-mail. At block 414, analytic export tool 102 may export a data package using e-mail.

Figure 5:
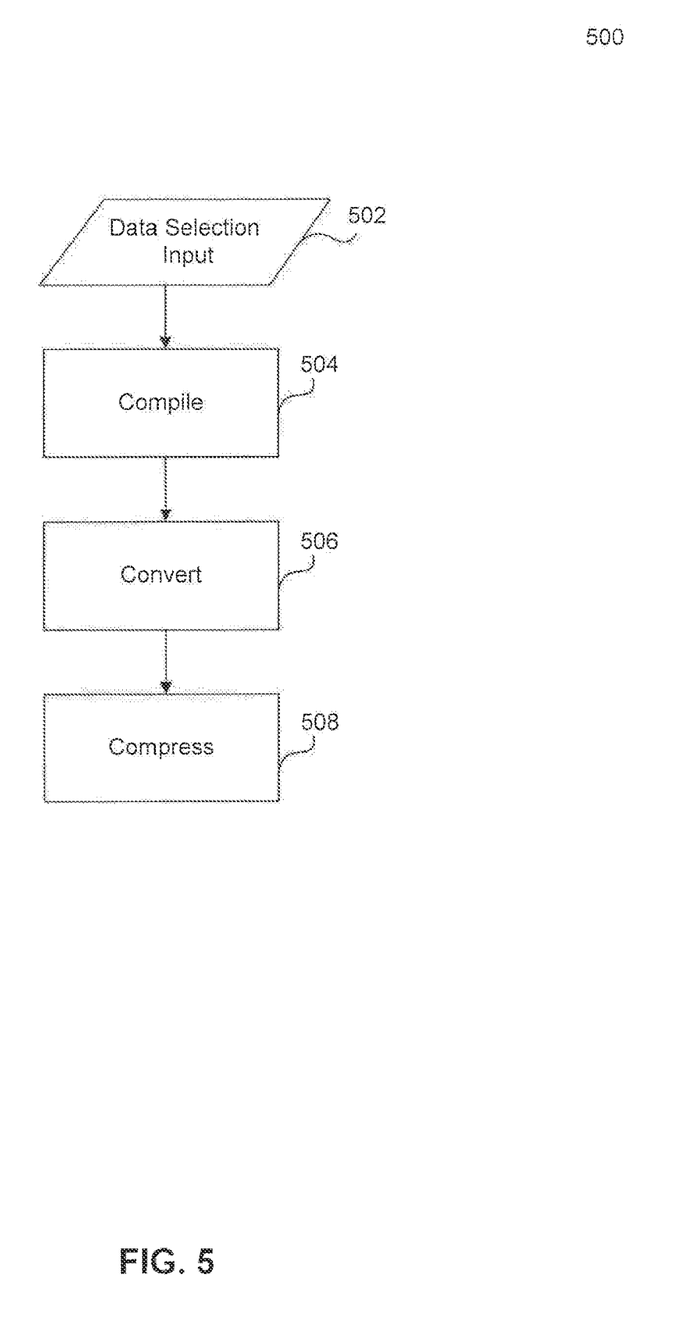
FIG. 5 shows an example flowchart illustrating a process for packaging analytic data from an application according to an embodiment.

FIG. 5 shows an example flowchart illustrating a process for packaging selected analytic data from an application according to an embodiment. At block 502, GUI 304 visualizes and displays a plurality of available analytic data and receives a data selection input comprising a selection of the available analytic data. For example, if a plurality of analytic data comprising dashboard A, dashboard B, dataset A, and dataset B are displayed by GUI 304, GUI 304 may receive a data selection input comprising the selections of dashboard B and dataset B.

At block 504, packager 308 may compile the analytic data into a data package according to the selection of the data selection input. For example, after a data selection input comprising the selections of dashboard B and dataset B is received by GUI 304, packager 308 may compile the data of dashboard B and dataset B into a data package. In an embodiment, compiling the selected analytic data into a data package may comprise arranging the selected analytic data according to metadata stored in memory 310. The metadata may comprise a prescribed order for analytic data required for exportation.

At block 506, packager 308 may convert the data package into any desired file type. For example, after a data package has been compiled comprising dashboard B and dataset B, the data package may then be converted into a desired file type, such as a BIT file—to name one example.

At block 508, packager 308 may compress the converted data package into a compressed file format. For example, the converted data package comprising dashboard B and dataset B may be compressed into any compressed file format such as 7Z, RAR, or ZIP—to name a few.

Figure 6:
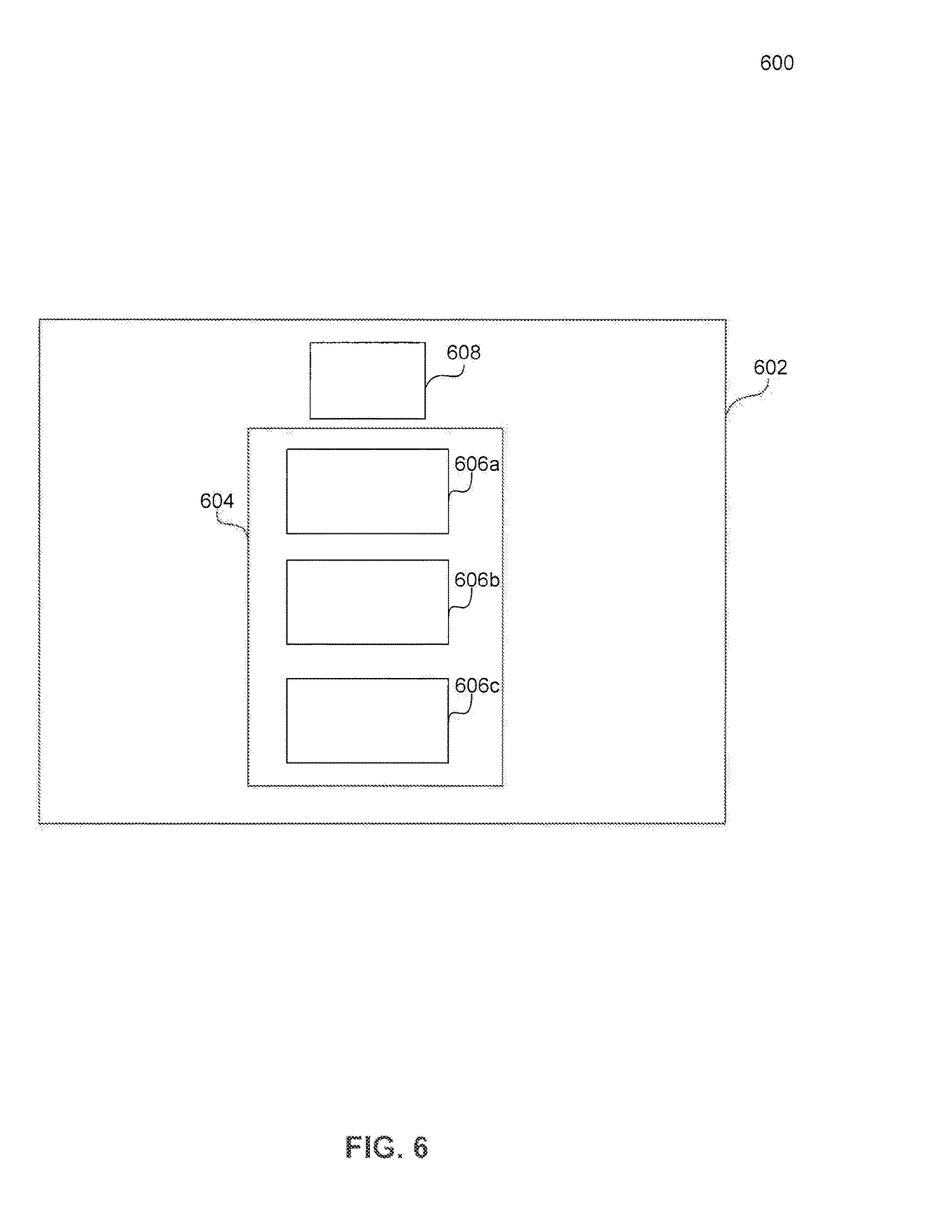
FIG. 6 shows an example graphical user interface (GUI) for exporting analytic data from an application according to an embodiment.

FIG. 6 illustrates an example GUI for exporting analytic data from an application according to an embodiment. Example GUI 602 may comprise a list of applications 604 and an export request button 608.

In an embodiment, the list of applications 604 may comprise a plurality of applications 606 (comprising applications 606a, 606b, and 606c) that may collect, create, store, or modify analytic data. When an interaction occurs with an application displayed in the list of applications 604, an export button 608 may be displayed. These interactions may comprise mouse clicks, mouse drags, or gestures made on a touch screen—to name a few According to an embodiment, export button 608 may then be interacted with by mouse clicks, mouse drags, or gestures made on a touch screen. The interactions with the plurality of applications 606 displayed in, the list of applications 604 and export button 608 may comprise an export input.

Figure 7:
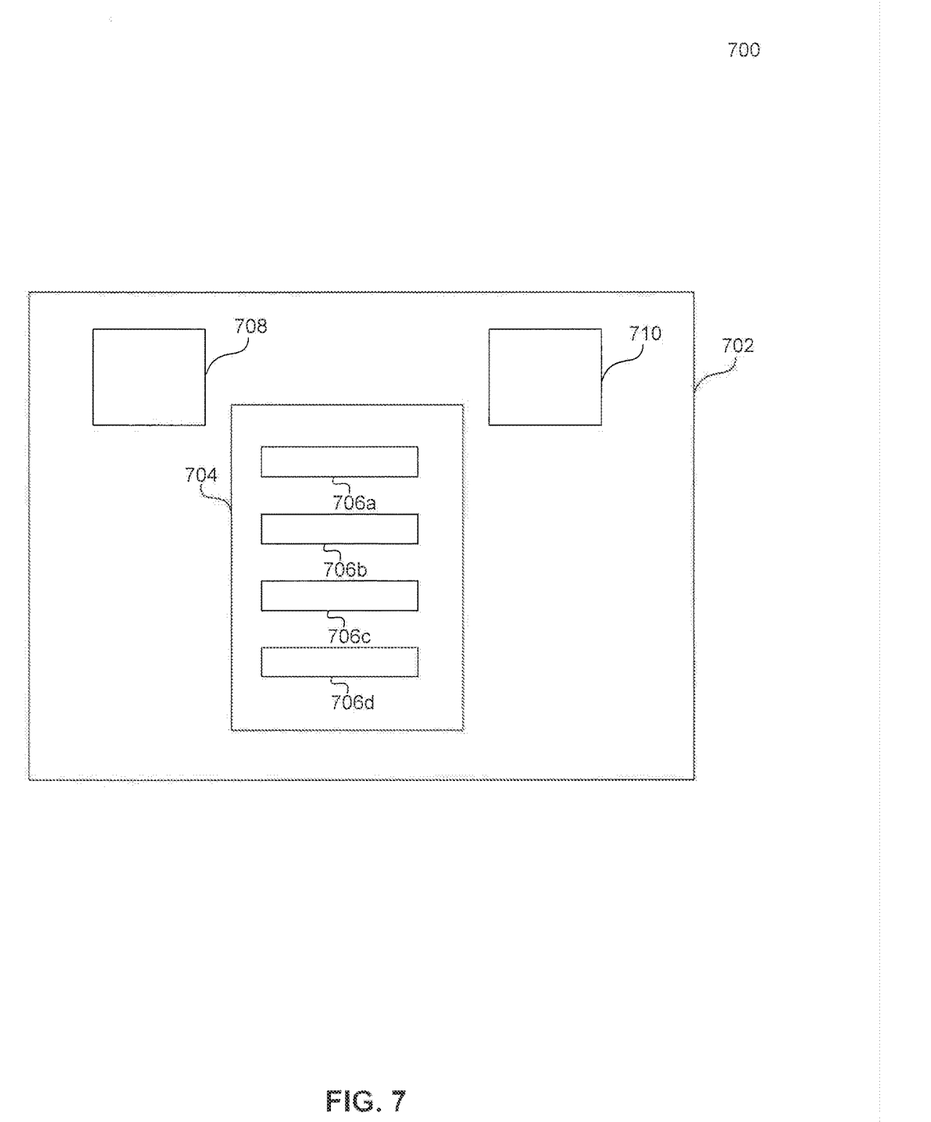
FIG. 7 shows an example GUI for exporting analytic data from an application according to an embodiment.

FIG. 7 illustrates an example GUI for exporting analytic data from an application according to an embodiment. According to an embodiment, GUI 702 may comprise a list of available analytic data 704, cancel button 708, and export button 710.

In an embodiment, the list of available analytic data 704 may comprise a plurality of available analytic data 706 (comprising analytic data 706a, 706b, 706c, and 706d) that may comprise datasets, tables, lists, lenses, and dashboards that have been collected, created, or modified by application 306 and stored in memory 310. GUI 702 may receive interactions with the plurality of available analytic data 706 displayed in the list of available analytic data 704. These interactions may comprise mouse clicks, mouse drags, or gestures made on a touch screen—to name a few.

In an embodiment, GUI 702 may comprise cancel button 708 and export button 710. GUI 702 may receive interactions with cancel button 708 and export button 710. These interactions may comprise mouse clicks, mouse drags, or gestures made on a touch screen to name a few. The interactions with the plurality of available analytic data 706 displayed in the list of available analytic data 704, cancel button 708, and export button 710 may comprise the data selection input.

Figure 8:
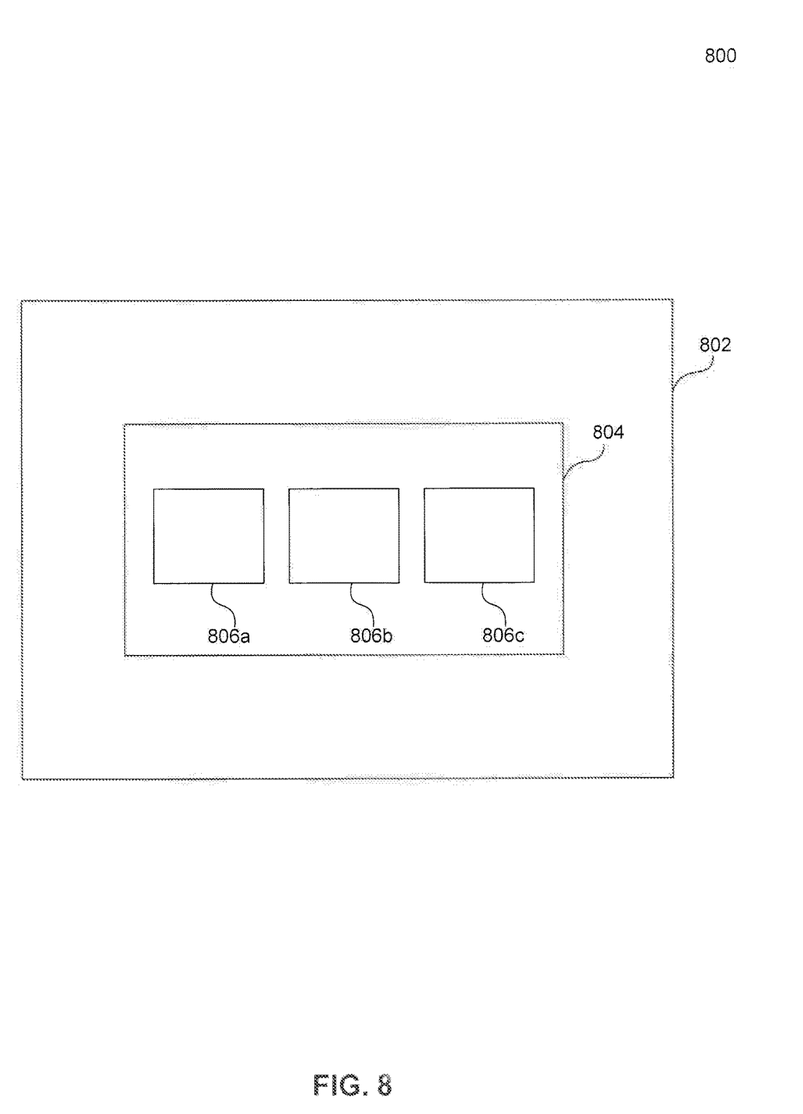
FIG. 8 shows an example GUI for exporting analytic data from an application according to an embodiment.

FIG. 8 shows an example GUI for exporting analytic data from an application according to an embodiment. GUI 802 may comprise a list of export options 804.

According to an embodiment, GUI 802 may comprise a list of export options 804 comprising a plurality of export options 806 (comprising export options 806a, 806b, and 806c) such as e-mail, text message, applications, and cloud storage—to name a few. GUI 802 may receive interactions with the plurality of export options 806 displayed in the list of export options 804. These interactions may comprise mouse clicks, mouse drags, or gestures made on a touch screen—to name, a few. The interactions with the plurality of export options 806 displayed in the list of export options 804 may comprise the export option selection input.

Various embodiments can be implemented, for example, using, one or more well-known computer systems, such as computer system 900 shown in FIG. 6. Computer system 900 can be any well-known computer capable of performing the functions described herein.

Figure 9:
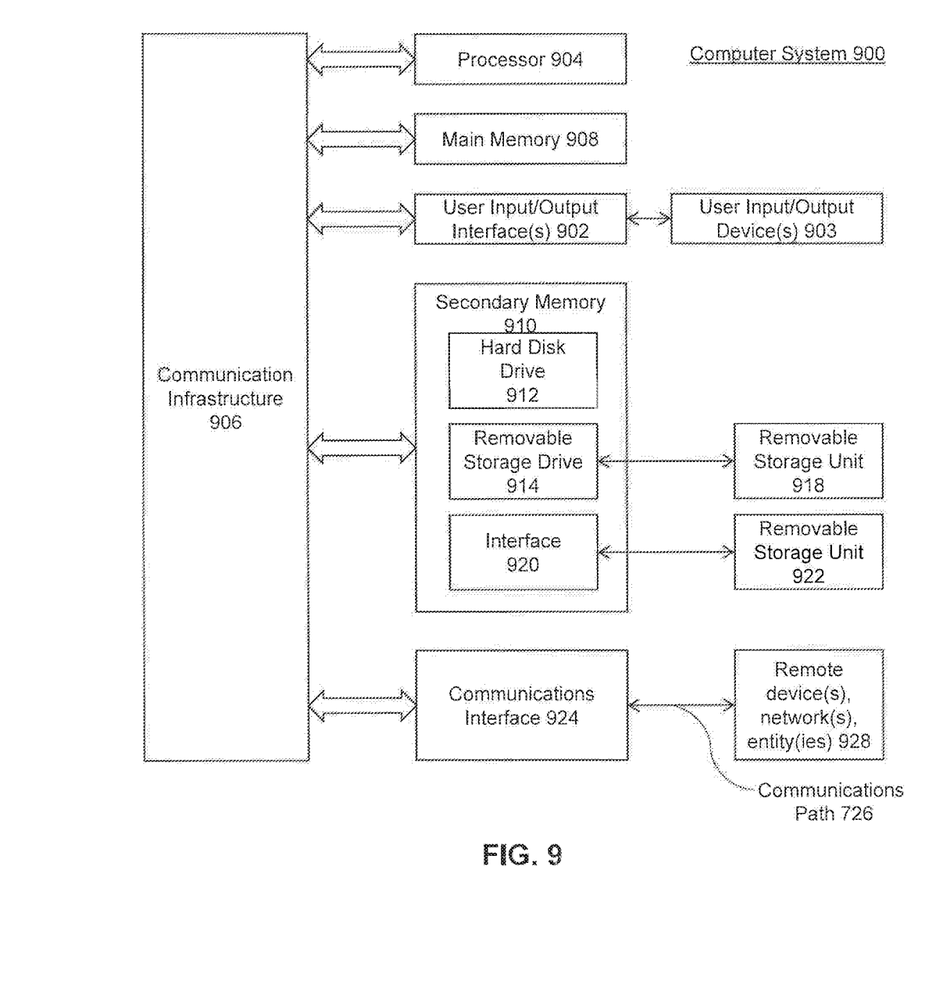
FIG. 9 is an example computer system useful for implementing various embodiments.

Computer system 900 includes one or more processors (also called central processing units, or CPUs), such as a processor 904. Processor 904 is connected to a communication infrastructure or bus 906.

One or more processors 904 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 900 also includes user input/output device(s) 903, such as monitors, keyboards, pointing devices, etc., that communicate with communication infrastructure 906 through user input/output interface(s) 902.

Computer system 900 also includes a main or primary memory 908, such as random access memory (RAM). Main memory 908 may include one or more levels of cache. Main memory 908 has stored therein control logic (i.e., computer software) and/or data.

Computer system 900 may also include one or more secondary storage devices or memory 910. Secondary memory 910 may include, for example, a hard disk drive 912 and/or a removable storage device or drive 914. Removable storage drive 914 may be a floppy disk drive, a magnetic tape drive, a compact disk drive, an optical storage device, tape backup device, and/or any other storage device/drive.

Removable storage drive 914 may interact with a removable storage unit 918.

Removable storage unit 918 includes a computer usable or readable storage device having stored thereon computer software (control logic) and/or data Removable storage unit 918 may be a floppy disk, magnetic tape, compact disk, DVD, optical storage disk, and/any other computer data storage device. Removable storage drive 914 reads from and/or writes to removable storage unit 918 in a well-known manner.

According to an exemplary embodiment, secondary memory 910 may include other means, instrumentalities or other approaches for allowing computer programs and/or other instructions and/or data to be accessed by computer system 900. Such means, instrumentalities or other approaches may include, for example, a removable storage unit 922 and an interface 920. Examples of the removable storage unit 922 and the interface 920 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 900 may further include a communication or network interface 924.

Communication interface 924 enables computer system 900 to communicate and interact with any combination of remote devices, remote networks, remote entities, etc. (individually and collectively referenced by reference number 928). For example, communication interface 924 may allow computer system 900 to communicate with remote devices 928 over communications path 926, which may be wired and/or wireless, and which may include any combination of LANs, WANs, the Internet, etc. Control logic and/or data may be transmitted to and from computer system 900 via communication path 926.

In an embodiment, a tangible apparatus or article of manufacture comprising a tangible computer useable or readable medium having control logic (software) stored thereon is also referred to herein as a computer program product or program storage device. This includes, but is not limited to, computer system 900, main memory 908, secondary memory 910, and removable storage units 918 and 922, as well as tangible articles of manufacture embodying any combination of the foregoing. Such control logic, when executed by one or more data processing devices (such as computer system 900), causes such data processing devices to operate as described herein.

Based on the teachings contained in this disclosure, it will be apparent to persons skilled in the relevant art(s) how to make and use embodiments of the invention using data processing devices, computer systems and/or computer architectures other than that shown in FIG. 6. In particular, embodiments may operate with software, hardware, and/or operating system implementations other than those described herein.

It is to be appreciated that the Detailed Description, section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building, blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, blocks, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A computer implemented method, comprising:
displaying, by a computing device, a graphical user interface (GUI) having a first GUI portion displaying a first application and first analytic data within the first application and having a second GUI portion displaying a second application and second analytic data within the second application, wherein the first application and the second application correspond to an identifier indicating that the first application and the second application are enabled for use by a particular organization;

receiving, by the computing device, a data selection input from the first GUI portion, wherein the data selection input comprises an interaction with the first analytic data;

packaging, by the computing device and according to the data selection input, the first analytic data from the first application together with the second analytic data from the second application in a data package configured to display the first analytic data in an instance of the first application and the second analytic data in an instance of the second application in response to unpacking the data package, wherein the data package includes the identifier; and exporting, by the computing device, the data package according to one of a plurality of displayed export options displayed in the GUI.

2. The computer implemented method of claim 1, the packaging further comprising:
arranging the first analytic data and the second analytic data into a prescribed order.

3. The computer implemented method of claim 1, the packaging further comprising:
compressing the data package into a compressed file type.

4. The computer implemented method of claim 1, the exporting further comprising:
receiving an export option selection input, wherein the export option selection input may comprise one of the displayed plurality of export options.

5. The computer implemented method of claim 1, further comprising:
canceling the packaging of the first analytic data and the second analytic data; and
ceasing the display of the plurality of export options.

6. A system, comprising:
a memory; and
at least one processor coupled to the memory and configured to:
display a graphical user interface (GUI) having a first GUI portion displaying a first application and first analytic data within the first application and having a second GUI portion displaying a second application and second analytic data within the second application, wherein the first application and the second application correspond to an identifier indicating that the first application and the second application are enabled for use by a particular organization;
receive a data selection input from the first GUI portion, wherein the data selection input comprises an interaction with the first analytic data;
package, according to the data selection input, the first analytic data from the first application together with the second analytic data from the second application in a data package configured to display the first analytic data in an instance of the first application and the second analytic data in an instance of the second application in response to unpacking the data package, wherein the data package includes the identifier; and
export the data package according to one of a plurality of displayed export options displayed in the GUI.

7. The system of claim 6, the at least one processor configured to package, further configured to:
arrange the first analytic data and the second analytic data into a prescribed order.

8. The system of claim 6, the at least one processor configured to package, further configured to:

compress the data package into a compressed file type.

9. The system of claim 6, wherein to export the data package, the at least one processor is further configured to:
receive an export option selection input, wherein the export option selection input may comprise one of the displayed plurality of export options.

10. The system of claim 6, the at least one processor further configured to:
cancel the packaging of the first analytic data and the second analytic data.

11. A tangible, non-transitory computer-readable device having instructions stored thereon that, when executed by at least one computing device, causes the at least one computing device to perform operations comprising:
displaying a graphical user interface (GUI) having a first GUI portion displaying a first application and first analytic data within the first application and having a second GUI portion displaying a second application and second analytic data within the second application, wherein the first application and the second application correspond to an identifier indicating that the first application and the second application are enabled for use by a Particular organization;
receiving a data selection input from the first GUI portion, wherein the data selection input comprises an interaction with the first analytic data;
packaging, according to the data selection input, the first analytic data from the first application together with the second analytic data from the second application in a data package configured to display the first analytic data in an instance of the first application and the second analytic data in an instance of the second application in response to unpacking the data package, wherein the data package includes the identifier;
exporting the data package according to one of a plurality of displayed export options displayed in the GUI.

12. The non-transitory computer-readable device of claim 11, the packaging operation further comprising:
arranging the first analytic data and the second analytic data into a prescribed order.

13. The non-transitory computer-readable device of claim 11, the packaging operation further comprising:
compressing the data package into a compressed file type.

14. The non-transitory computer-readable device of claim 11, the exporting operation further comprising:
receiving an export option selection input, wherein the export option selection input may comprise one of the displayed plurality of export options.

15. The non-transitory computer-readable device of claim 11, the operations further comprising:
canceling the packaging of the first analytic data and the second analytic data; and
ceasing the display of the plurality of export options.

16. The computer implemented method of claim 1, wherein the first analytic data includes GUI instruction data to generate a dashboard and the second analytic data is a listed dataset.

17. The computer implemented method of claim 16, wherein the dashboard includes a subset of content from the listed dataset and wherein the packaging further comprises:
in response to receiving the data selection input, automatically selecting the subset of content from the second analytic data.

18. The system of claim 6, wherein the first analytic data includes GUI instruction data to generate a dashboard and the second analytic data is a listed dataset.

19. The system of claim 18, wherein the dashboard includes a subset of content from the listed dataset and wherein, to package the first analytic data and the second analytic data, the at least one processor is further configured to:
in response to receiving the data selection input, automatically select the subset of content from the second analytic data.

20. The non-transitory computer-readable device of claim 11, wherein the first analytic data includes GUI instruction data to generate a dashboard and the second analytic data is a listed dataset.

21. The non-transitory computer-readable device of claim 20, wherein the dashboard includes a subset of content from the listed dataset and wherein the packaging further comprises:
in response to receiving the data selection input, automatically selecting the subset of content from the second analytic data.

22. The computer implemented method of claim 1, wherein the first application and the second application are hosted by a multi-tenant system and the multi-tenant system maintains the identifier, the packaging further comprising:
in response to the receiving, retrieving, by the computing device, the first analytic data, second analytic data, and the identifier from memory of the multi-tenant system.

23. The non-transitory computer-readable device of claim 11, wherein the first application and the second application are hosted by a multi-tenant system and the multi-tenant system maintains the identifier, the packaging further comprising:
in response to the receiving, retrieving, by the computing device, the first analytic data, second analytic data, and the identifier from memory of the multi-tenant system.

* * * * *

UNITED STATES PATENT AND TRADEMARK OFFICE
CERTIFICATE OF CORRECTION

PATENT NO. : 10,437,440 B2
APPLICATION NO. : 15/052580
DATED : October 8, 2019
INVENTOR(S) : Kim et al.

Page 1 of 1

It is certified that error appears in the above-identified patent and that said Letters Patent is hereby corrected as shown below:

In the Claims

Claim 11, Column 13, Line 23, please replace "a Particular organization;" with --a particular organization;--.

Signed and Sealed this
Fifth Day of May, 2020

Andrei Iancu
*Director of the United States Patent and Trademark Office*